United States Patent [19]
Haberman

[11] Patent Number: 5,888,216
[45] Date of Patent: Mar. 30, 1999

[54] PROSTHESIS LINER FOR BELOW-KNEE AMPUTEES

[76] Inventor: Louis J. Haberman, 1 Arden Rd., Denville, N.J. 07834

[21] Appl. No.: 738,278

[22] Filed: Oct. 25, 1996

Related U.S. Application Data

[63] Continuation-in-part of Ser. No. 617,392, Mar. 18, 1996, abandoned.

[51] Int. Cl.$^6$ ........................................................ A61F 2/78
[52] U.S. Cl. ................................................................ 623/36
[58] Field of Search ............................. 623/32–37, 57; 602/62

[56] References Cited

U.S. PATENT DOCUMENTS

| | | | |
|---|---|---|---|
| 2,244,871 | 6/1941 | Guinzburg | 2/59 |
| 3,322,873 | 5/1967 | Hitchcock | 264/222 |
| 3,377,416 | 4/1968 | Kandel | 264/222 |
| 3,600,717 | 8/1971 | McKeehan . | |
| 3,957,713 | 5/1976 | Jeram et al. | 524/703 |
| 4,300,245 | 11/1981 | Saunders | 623/35 |
| 4,413,359 | 11/1983 | Akiyama et al. | 623/36 X |
| 4,822,371 | 4/1989 | Jolly et al. | 623/32 |
| 4,908,037 | 3/1990 | Ross | 623/32 |
| 4,923,474 | 5/1990 | Klasson et al. | 623/33 |
| 5,007,937 | 4/1991 | Fishman et al. | 623/34 |
| 5,163,965 | 11/1992 | Rasmusson et al. | 623/36 |
| 5,226,918 | 7/1993 | Silagy et al. | 623/32 |
| 5,246,464 | 9/1993 | Sabolich | 623/33 |
| 5,263,990 | 11/1993 | Handal | 623/57 |
| 5,314,497 | 5/1994 | Fay et al. | 623/34 |
| 5,376,131 | 12/1994 | Lenze et al. | 623/34 |
| 5,507,834 | 4/1996 | Laghi . | |
| 5,603,122 | 2/1997 | Kania | 2/239 |
| 5,662,715 | 9/1997 | Slemker | 623/36 |

FOREIGN PATENT DOCUMENTS

| | | | |
|---|---|---|---|
| 712847 | 10/1931 | France | 623/57 |
| 391185 | 3/1924 | Germany | 623/57 |
| 609573 | 2/1935 | Germany | 623/57 |
| 53-31750 | 3/1978 | Japan | 623/33 |
| WO 95/31160 | 11/1992 | WIPO . | |
| WO 95/05792 | 3/1995 | WIPO . | |

OTHER PUBLICATIONS

Kubota et al., Photokilling of T–24 human bladder cancer cells with titanium dioxide, Br. J. Cancer, 70, 1107–1111 1994.

*Primary Examiner*—David H. Willse
*Attorney, Agent, or Firm*—Paul N. Katz

[57] ABSTRACT

A prosthesis liner for below-knee amputees comprising a polymer liner, such as silicone, incorporating a pre-flexed shape having an angle at the knee selected from 20 to 60 degrees, at least one thickened upper silicone band, an appropriate anatomical shape and taper and a flexible connector piece at the bottom portion of the liner adapted for connection to a walking piece. An anti-bacterial agent is added to the liner to suppress the over-growth of bacteria that may form between the liner and the residuum.

12 Claims, 3 Drawing Sheets

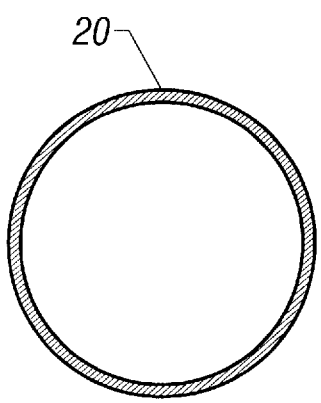
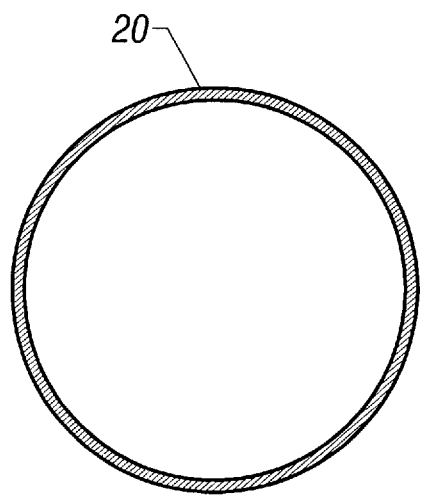
FIGURE 3
FIGURE 4
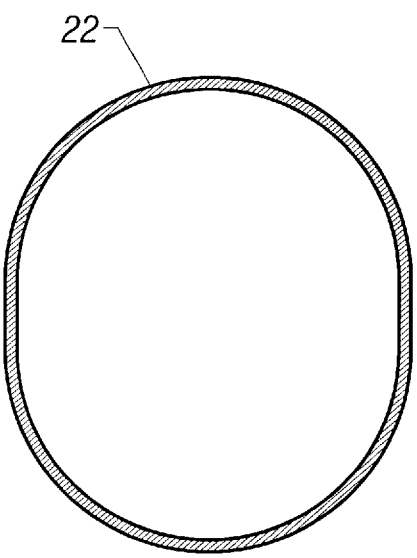
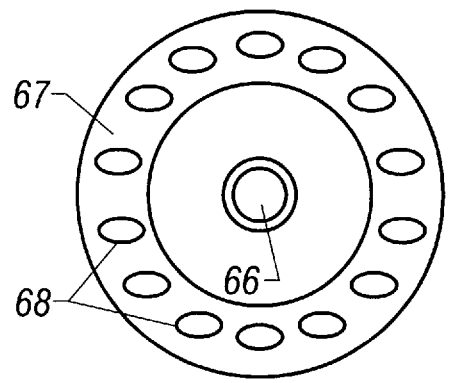
FIGURE 5
FIGURE 7

PROSTHESIS LINER FOR BELOW-KNEE AMPUTEES

CROSS REFERENCE TO RELATED PATENT APPLICATION

This patent application is a continuation-in-part of U.S. patent application Ser. No. 08/617,392, filed Mar. 18, 1996, now abandoned, entitled "Prothesis Method and Device For Below-Knee Amputees" by Louis J. Haberman, and is incorporated by reference herein.

FIELD OF THE INVENTION

The invention generally relates to prosthesis devices and, in particular, the invention relates to a prosthesis device liner incorporating a preflexed angle at the knee.

BACKGROUND OF THE INVENTION

The prior art prosthesis utilizing a below-knee silicone liner is described in detail in various prosthetic journals. In 1989, C. H. Fillauer, CPO, C. H. Pritham, CPO, and K. D. Fillauer, CPO, reported on "The Evolution and Development of the Silicone Suction Socket (3S) for Below-Knee Prostheses" in the *Journal of Prosthetics and Orthotics*. In 1995, L. J. Haberman, CPO, R. A. Bedotto, CPO, LPT, and E. J. Colodney, MD, described the use of an injection-molded silicone liner with suspension tabs for below-knee amputees in the article entitled "Silicone Only Suspension" (SOS) in the *Journal of Prosthetics and Orthotics*.

The prior art below-knee silicone designs are constructed either of fabric impregnated with silicone or with room temperature vulcanized (RTV) silicone. The fabric-type liner is conventionally laminated with a liquid silicone (RTV) under a vacuum-type system. These liners have the disadvantage that they are porous and harbor and promote the growth of bacteria. Further, the fabric silicone liner lacks durability when the thin silicone material is subject to abrasion during daily use since it rubs against the residuum (stump) which eventually uncovers the underlying fabric which can irritate the skin.

Other RTV silicone liners have been disclosed in the prior art which are custom injection-molded. While these silicone liners are relatively non-porous and cannot harbor bacteria, they are inclined to be fragile, reducing their service life, and are also time-consuming to fabricate.

Pre-fabricated injection-molded silicone liners are now available to the amputee in various sizes and styles. They are more durable as they are constructed of a heat-cured, two part silicone composition. They are constructed free of a fabric matrix and, thus, will not irritate the skin as the inner surface is rubbed away. All of these commercially available silicone liners are, however, generally tubular in shape, offering very little tapering towards the distal end. Such silicone liners are in a straight-line orientation (windsock shaped) and respond poorly to angular (flexion) changes to the knee. As an illustration, significant wrinkling of these straight-line silicone liners occur in the back of the knee when the user sits down. Heightened compression of the kneecap (patella) occurs which can irritate the skin overlying the kneecap. Straight-line oriented liners also tend to bias the knee joint to a straight position when the knee is flexed, i.e., the liner is under tension and it wants to restore itself to its straight molded position. Thus, the amputee must maintain a flexure pressure in order to keep the knee and prosthesis from extending to its straight position.

Silicone liners typically utilize a hard, unyielding material, such as aluminum or polycarbonate as a shuttle screw housing (hereafter "umbrella") for affixing the lower leg portion of the prosthesis. Rigid aluminum shuttle screw housings and rigid polycarbonate shuttle screw housings are not flexible and have limitations as to functional life and/or comfort to the amputee. Polycarbonate umbrellas may fracture and fail within months of initial use. Aluminum umbrellas have no flexibility and cannot distort to comply with the naturally occurring movement of the residuum within the prosthetic socket.

Prior art silicone liners also lack anatomical symmetry to the amputation limb which results in marked distortion of the silicone liner during naturally occurring changes in the position of the knee and residuum. The lack of anatomical symmetry results in a reduction of the naturally occurring range of motion (ROM) present in the human knee due to the wrinkling and bunching of the silicone material in that region. The lack of anatomical symmetry causes an uneven stretching of the silicone liner which may be harmful to the underlying tissues, be uncomfortable to wear, and can result in premature wearing and subsequent tearing of the silicone liner. Prior art silicone liners lack reinforcement at their upper (proximal) edge which may result in premature tearing, requiring early replacement of the silicone liner.

Silicone liners also create conditions which increase the potential for growth of bacteria on the skin of the amputee. The silicone liner, which is a relatively impermeable material, tends to encourage the skin to be constantly moist from sweating. This condition creates the right environment for undesirable bacteria to proliferate on the residuum, thus making the amputee's skin susceptible to invasion by pathogenic microorganisms. The constant moisture present when wearing a silicone liner and the occlusion from the liner which occurs to the amputee's skin, increases the skin's vulnerability to bacteriological infection.

OBJECTS OF THE INVENTION

An object of the invention is to provide a prosthesis device with a polymer liner incorporating a pre-flexed angle at the knee.

Another object of the invention is to provide such a liner with at least one thickened silicone band toward the upper (proximal) edge of the liner.

Another object of the invention is to provide such a liner with at least two thickened silicone bands toward the upper (proximal) edge of the liner.

A further object of the invention is to provide a prosthesis with a liner having an appropriate anatomical shape and taper.

A still further object of the invention is to provide a flexible connector piece for prosthesis suspension positioned at the bottom (distal) portion of the prosthesis device.

Another object of the invention is to incorporate an anti-bacterial agent or agents into the liner which substantially suppresses the over-growth of bacteria between the liner and the residuum.

Yet another object of the invention is to provide and incorporate a umbrella made of flexible material, such as silicone, at the distal end of the silicone liner for attaching a rod which is used as part of a prosthesis to enable the amputee to walk thereon.

Other objects and the advantages of the invention will appear from the following description.

SUMMARY OF THE INVENTION

It has been discovered that the utilization of a prosthesis which incorporates a pre-flexed angle of from 20 to 60 degrees at the knee region results in better comfort for the user and extends the service life of the prosthesis. The flexed angle of the present invention substantially reduces wrinkling of the liner behind the knee when the knee is flexed. In addition, the kneecap (patella) is not overly compressed by the silicone material of the liner when the knee is flexed. Skin irritation, blister formation and discomfort to the back of the knee and the kneecap are thus substantially reduced when using the present invention. Also, the pre-flexed silicone liner permits far greater knee flexion for the amputee then was possible with the prior art straight liners. This is important to the basic activities of daily living. This feature also is helpful in such circumstances as sitting for periods greater than 15 minutes, getting in and out of a car, sitting in a movie theater, avoiding the necessity for an aisle seat on an airplane and the like.

A feature of the present invention is a thickened upper portion of the wall of the silicone liner which significantly reduces tearing of the silicone liner that most often occurs when donning and doffing it. The thickened upper portion of the silicone liner also creates a proximal radius which is helpful in reducing the incidence of shear to stress loading of the skin proximate thereto.

Another feature is the pre-flexed angle which minimizes wrinkling behind the knee, increases the range of motion of the knee joint, and is more comfortable to wear when sitting.

Another feature is an anatomical taper which achieves more uniform compression of the skin of the residuum.

Still another feature is at least one proximal silicone band which reduces tearing, provides a radius to reduce skin shear, and improves the suction seal of the liner to the residuum.

Still another feature of the present invention is at least two proximal silicone bands which reduce tearing, provide a radius to reduce skin shear, and improve the suction seal of the liner to the residuum. In addition the proximate end of the liner may be trimmed between the at least two silicone bands to reduce the length of the liner for improved comfort of the amputee without compromising the aforementioned features of the present invention.

Another object of the invention is to incorporate an anti-bacterial agent or agents into the silicone liner which substantially suppresses the over-growth of bacteria between the liner and the residuum.

Yet another object of the invention is to provide and incorporate a umbrella made of flexible material, such as silicone, at the distal end of the liner for attaching a rod which is used as part of a prosthesis to enable the amputee to walk thereon.

In an embodiment of the present invention, the thickened upper portion of the wall of the silicone liner may be comprised of a plurality of bands molded into the upper portion thereof. At least two of these bands may be employed so that the liner can be trimmed between the bands if the liner is uncomfortable to the person wearing it because the upper portion of the liner may ride too high on the thigh. Preferably, the bands may be spaced ¾ inch apart. The second band also strengthens the liner wall which increases durability of the liner and thus its useful life. The second band also improves the seal of the liner while reducing the shear strain on the skin of the wearer.

The anatomical shape and distal taper approximates the naturally occurring shape of the amputation limb. This anatomical correctness greatly enhances overall comfort and offers far more uniform and appropriate compression to the soft underlying tissues. The anatomical shape and distal taper of the silicone liner offers the wearer a pre-fabricated fit on a par with those utilizing an expensive, custom made silicone liner. The availability of many circumferential sizes and shapes will accommodate the vast majority of amputation shapes. The anatomical shape and distal taper of the silicone liner reduces the potential for uneven stretching, thus prolonging the useful life of the liner and enhancing the comfort of the wearer.

A further embodiment of this invention incorporates an anti-bacterial agent or several anti-bacterial agents in combination, into the silicone material to inhibit over-population of naturally occurring skin bacteria. It is thought, in light of the large population of bacteria present on the skin, that these normally occurring skin bacteria are generally harmless microorganisms that are physiologically beneficial. These normally occurring skin bacteria are found in hair follicles and in moist intertriginous locations. Conditions, which encourage the skin to be constantly moist from sweating, occluded (by a relatively impermeable material, such as a silicone liner) and immersed, will make it extremely susceptible to invasion by pathogenic microorganisms. Two of the aforementioned conditions, which increase the skin's vulnerability to bacteriological infection, are always present when an amputee utilizes a prosthetic silicone liner, that is, constant moisture and occlusion.

Skin dryness of the residuum (stump) and good hygiene (frequent cleansing with a mild detergent) are the principal mechanisms for prevention of bacteriological over-population. Although variable (significant to minimal), there is always some level of moisture present, from perspiration, on the residuum when a prosthetic silicone liner is worn. Good hygiene via frequent washing of the residuum during the day is difficult and inconvenient for the amputee. Since the environment within the prosthetic silicone liner is so conducive to the marked proliferation of bacteria and the increased probability of infection (folliculitis), the incorporation of a low-level, time-released, anti-bacterial agent or agents into the silicone material, suppresses such an over-population of bacteria and the potential for infection of the residuum. Folliculitis, furuncles, carbuncles and other bacteriological infections are commonplace for an amputee, particularly a lower-limb amputee.

Anti-bacterial agents, such as "NEOSPORIN," "BACITRACIN" and "SILVEDENE" are prepared by pharmaceutical chemists under appropriate and industry standard conditions. Newer, and possibly more beneficial, anti-bacterial agents may also be utilized in this manner as they become available. A solution of the anti-bacterial agent or agents in combination are mixed into either the Part A, Part B or both of the containers of the two-part silicone material prior to injection of the silicone into the prosthetic mold, which when cured, forms the prosthetic silicone liner. The concentrations of the anti-microbial agent(s) are substantially lower than the concentration one would receive from a topical application of the same or similar agent. For instance, if a topical anti-bacterial cream contains a 5% concentration of erythromycin or dicloxacillin, then the prosthetic silicone liner will only permit levels of such agents reaching the skin to achieve that of a portion of 1% and up to 2% of that agent's concentration. Of importance, is that the intent of this embodiment is to control or reduce the over-population of naturally occurring bacteria via a controlled low-level, time-released anti-bacterial agent(s) within a prosthetic silicone liner which is highly conducive to bacteriological over-population and subsequent bacteriological infection. It is not the intent of this embodiment to treat or cure bacteriological infections.

The curing of silicones (polymers) results in the formation of three dimension chemical structures to which anti-bacterial agents may join. The chemical composition of the polymer may be altered to effect precise control of the release of the anti-bacterial agents. As prosthetic silicone liners typically have a useful life of only six months to one year, it is envisioned that the anti-bacterial agent(s), contained within its silicone structure, offer a similar time of release. The moisture from perspiration always present on the residuum (within the prosthetic silicone liner) actually serves as the vehicle to move the anti-bacterial agent(s) from the silicone material to the skin in order to control bacteriological over-population. Without moisture (a solution) the anti-bacterial agent(s) would never reach the skin of the residuum. The movement of the anti-bacterial agent(s) from the prosthetic silicone liner to the residuum occurs as a consequence of entropy, that is, the anti-bacterial agent(s) will move from areas of greater concentration (within the silicone) to areas of lesser concentration (the skin).

A metal umbrella, typically made of aluminum, may be installed in the thickened distal end of the silicone liner for attachment of a walking piece to the liner and residuum socket. A preferred embodiment, however, of the present invention uses a flexible umbrella that is installed in the thickened distal end of the silicone liner. This flexible umbrella is made of a flexible material such as silicone, and is an improvement over the aluminum and polycarbonate umbrellas. The flexible umbrella of the present invention does not fracture as does the polycarbonate types and it bends and flexes, unlike the metal umbrella, with the soft, distortable silicone liner material which further enhances distal limb comfort.

Other and further objects, features and advantages will be apparent from the following description of presently preferred embodiments of the invention, given for the purpose of disclosure and taken in conjunction with the accompanying drawings.

BRIEF DESCRIPTION OF THE DRAWINGS

FIG. 3 is cross sectional view taken alone line 3, 3 of FIG. 1;

FIG. 4 is cross sectional view taken alone line 4, 4 of FIG. 1;

FIG. 5 is cross sectional view taken alone line 5, 5 of FIG. 1;

FIG. 7 is an enlarged frontal view of the face of the umbrella fixture illustrated in FIG. 6.

DESCRIPTION OF THE PREFERRED EMBODIMENTS

Figure 1:
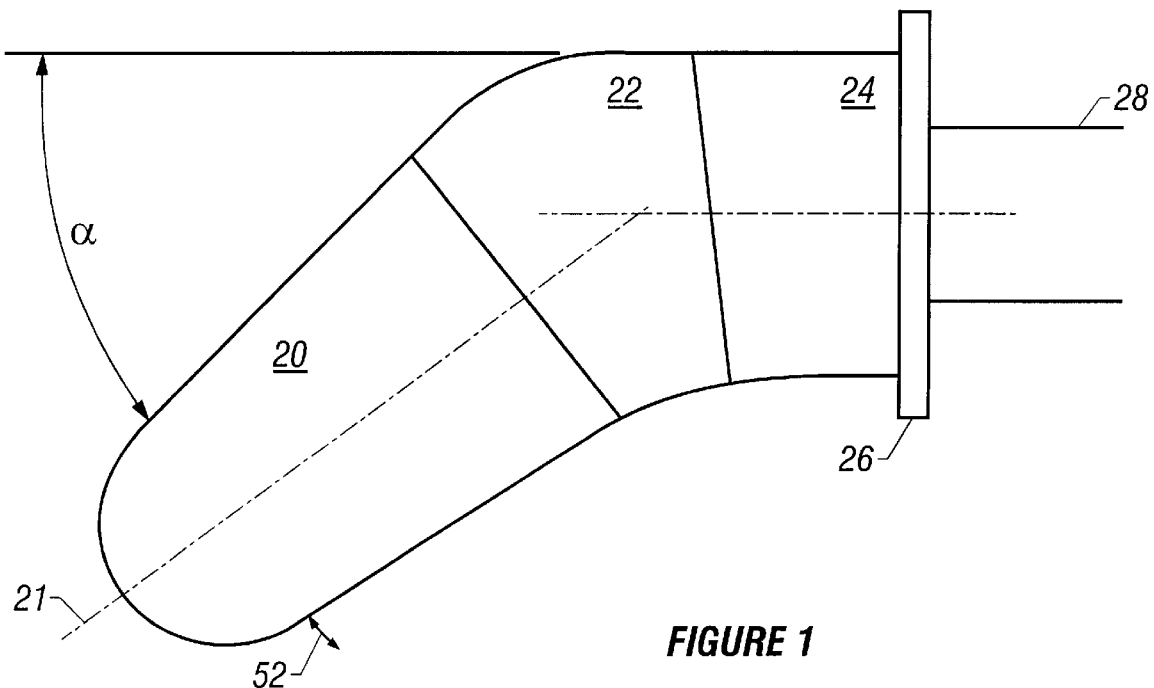
FIG. 1 is a elevational view of a core for fabricating a prosthesis made in accordance with the present invention.
Figure 2:
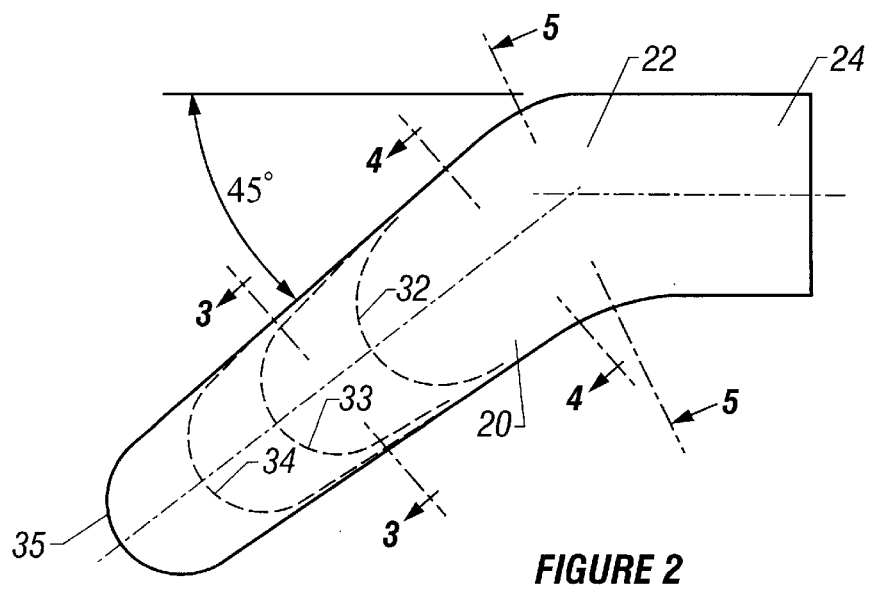
FIG. 2 is an elevational view illustrating different lengths of the core made in accordance with this invention.

Referring now to the drawings, the details of the preferred embodiments of the present invention are schematically illustrated. Like elements in the drawings will be represented by like numbers, and similar elements will be represented by like numbers with a different lower case letter suffix. Referring now to FIG. 1, a core is generally indicated by the numeral 10. The core is preferably formed of aluminum in two or three sections. The three section core comprises a lower third module 20, a knee module 22 and an upper third module 24. The two section core combines the knee module 22 and upper third module 24 into one machined unit module. The two section core eliminates one joint seam which would normally appear on the inside of the silicone liner fabricated therefrom. A center line 21 represents the mid point of each of the modules 20, 22 and 24. An alignment ring 26 is provided at the top of the upper third module 24. A locking key 28 is affixed at the top of the upper third module 24. The lower third module 20 extends from the knee module 22 at an angle α, where the angle α may be selected from 20 to 60 degrees. As illustrated in FIG. 2, the length of the lower third module 20 can have various lengths 32, 33, 34 or 35 depending on the condition of the limb on which the prosthesis is to be used. Cross sections of the aluminum core 10 are illustrated in FIGS. 3, 4 and 5.

Figure 6:
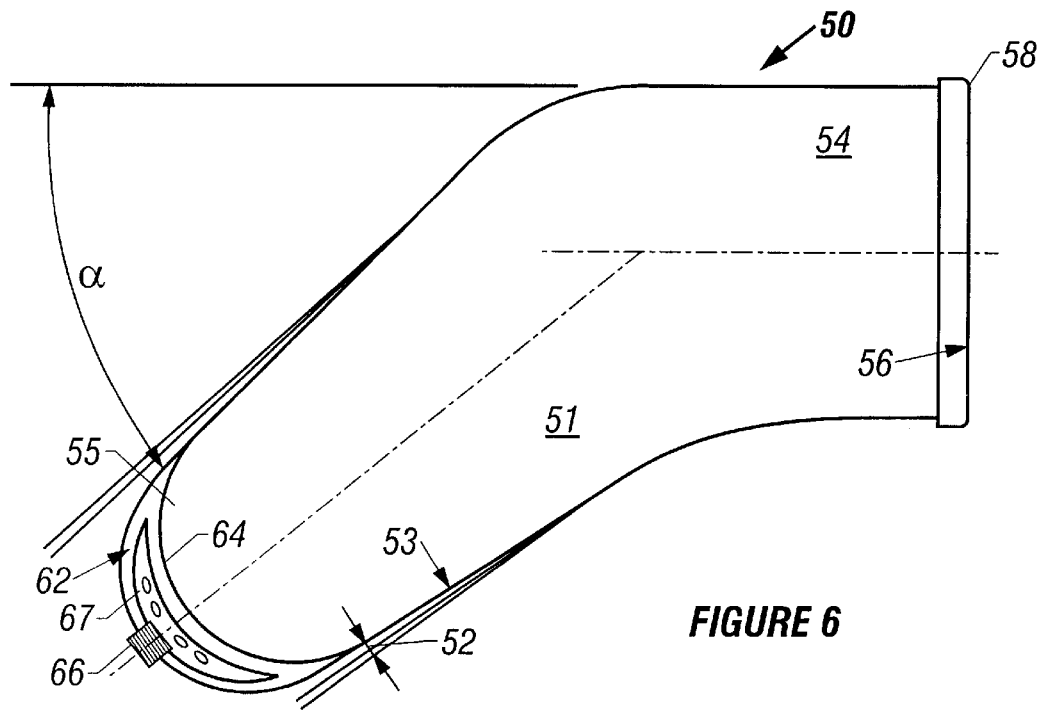
FIG. 6 is a elevational view of a prosthesis made in accordance with this invention showing the use of an umbrella fixture.

Referring now to FIG. 6, a prosthesis liner according to the present invention is generally indicated by the numeral 50 and is preferably made of silicone polymer formed over the metal core 10 (illustrated in FIG. 1) by placing and securing the metal core 10 into a female mold (not illustrated). The liner 50 has the same general shape as the aluminum core 10 and has the same flexed angle α which may be from 20 to 60 degrees. The liner 50 has a thickened band 56 around its top or upper part 54. The thickened band 56 has a rounded radius 58 on its top edge. The lower end 55 of the liner 50 has an anatomical taper 53 so the cross section of the liner 50 decreases from its approximate midpoint 51 to its lower end 55. The taper 53 angle, indicated by the numeral 52, may be from 5 to 12 degrees. An attaching means generally indicated by the numeral 62 is provided at the lower end 55 of the liner 50 to allow a lower leg with foot portion or walking piece (not illustrated) to be affixed to a threaded coupling 66.

Referring now to FIG. 7, a frontal view of the face of attaching means 62 is illustrated in more detail. The attaching means 62 may take the form of an umbrella 67 shaped fitting or shuttle housing which conforms with the closed curvature 64 (FIG. 6) at the lower (distal) end 55 of the liner 50. The threaded coupling 66 of the umbrella 67 is adapted for attachment of a desired walking piece (not illustrated). The umbrella 67 is generally circular in shape with a series of oval openings 68, evenly spaced and extending around the circular shape of the umbrella 67. The umbrella 67 may be made from a metal such as aluminum, or preferably from a flexible material such as silicone.

Figure 8:
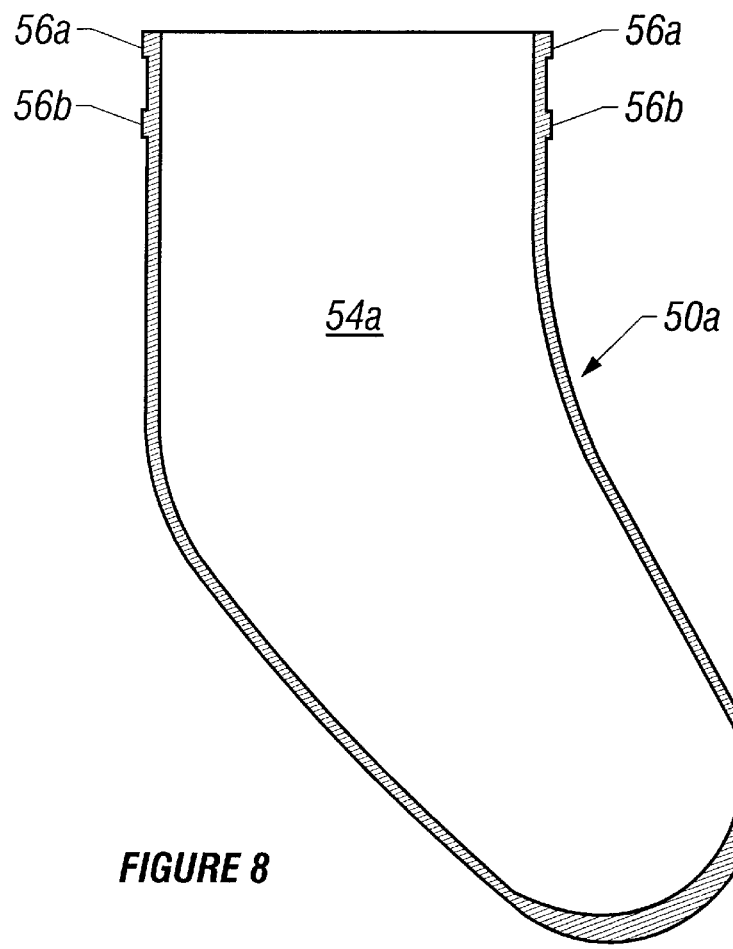
FIG. 8 is a cutaway elevational view of another prosthesis embodiment of this invention.

Referring to FIG. 8, a cutaway view of another embodiment of the present invention is illustrated. A liner 50a has at least two thickened bands 56a and 56b around its top or upper part 54a. The bands 56a and 56b are preferably spaced apart ¾ inch. The bands 56a and 56b enhance the seal between the liner and residuum and improve the durability of the liner and thus increase its useful life. In addition, the liner 50a may be trimmed between the bands 56a and 56b (removing the ¾ inch portion above band 56b of the upper portion 54a of the liner 50a, and the band 56a) to reduce the length of the liner over the thigh when there is discomfort to the wearer from the normal length of the upper part 54a.

In producing a prosthetic below-knee silicone liner in accordance with the present invention, a unique methodology has been employed. An initial core model, representing the actual shape and circumference of a particular size amputation limb, is initially sculpted in plaster of paris. The shape of this initial core model is representative of an amputation limb of which an initial plaster wrap impression is obtained from the actual amputation limb.

This amputation limb model is obtained in a selective manner. The limb model must be relatively uniform in shape and have present substantially no anatomical anomalies. Once obtained, a negative wrap cast is filled with a dental stone type plaster of paris. The negative wrap cast is removed, leaving only the positive plaster of paris model of the amputation limb. The model is reduced, in varying amounts, in all regions of the plaster model. The model is smoothed, blended and checked to confirm that a desired angle selected from a range of approximately 20 to 60 degrees, as measured from the intersection of two lines formed by an extended line from the front of the thigh to the long axis of the front of the remaining tibia. Further sculpting ensures that the distal third of the plaster model is tapered and rounded (FIG. 3), that the middle knee area is oval shaped (FIG. 5), and that the upper third of the plaster model is in a substantially rounded configuration. The plaster model also may be made in a neuter form, that is, neither left-sided nor right-sided. This is achieved artistically and is generally accurate, but may not be completely anatomically correct.

The plaster model is then measured and a computer added design ("CAD") representation of the model is produced. The left and right sides of the model are further detailed to produce a mirror image. All other features and goals for the shape of the model are performed via CAD techniques. The CAD model blueprint and mathematical relationships are transferred to a CNC machine. The core model is then cut from a large block of solid aluminum. A locking key 28 (see FIG. 1) is produced as part of the upper third of the model. When complete the solid core model is cut into three distinct sections (the lower third module 20, the knee module 22 and the upper third module 24). Each of the modules 20, 22, 24 is further machined internally. Holes are provided for later insertion of a heater core (not illustrated). Additional holes are made and tapped in order to bolt the individual modules 20, 22, 24 together.

This feature (sectional core modules) is necessary due to the pre-flexion angle α which may be selected from 20 to 60 degrees. As there now exists a clear delineation of the thigh and lower leg sections of the model, limb length becomes a consideration never before required by the prior art straight molds. The removable distal third section (module 20) of the core model will be interchanged with other distal third sections of various lengths. This is important as there exists a great variety of amputation limb lengths requiring that each of the various circumferentially sized core models offer this feature. All distal third core sections preferably are made in lengths of 4, 6, 8 and 10 inches, however, any length from 2 to 12 inches is feasible and contemplated herein. Each of the various length third core sections (module 20) are machined so as to properly fit the lower margin of the knee module 22 with a minimum of a seam.

Models having different cores of varying circumferences also may be manufactured in the aforementioned manner, each with additional distal third sections of the various lengths described. The model circumferences, as measured from 6 cm from the very distal end, may range in size, for example, from 10 cm to 30 cm, in increments of 2 cm.

The finished core models and the various additional length modules are polished and plated. Large blocks of aluminum are mathematically machined to create cavities inside the aluminum blocks (not illustrated) that precisely fit the core model and the upper key previously mentioned. The inner, negative cavity is then dimensionally increased by additional machining to create a 1.5 to 2 mm gap between the core model and the inner aspect of the aluminum block.

There are instances when below-knee amputees would desire and request a prosthetic silicone liner with the features of the current invention but with an alteration. Amputee athletes, some geriatric and other amputees of various ages might seek a thicker, softer and squashier prosthetic silicone liner. The alteration would require fabrication of a new core mold that is circumferentially smaller than the present one, which now creates a prosthetic silicone liner that is 1.5–2 mm thick. The new and smaller core mold would be created by a CNC lathes and other equipment. Machining would follow an identical tool path to the original core, only smaller, so that it creates a larger gap between the new core and the existing, unmodified female molds. This larger gap of 5–9 mm would create a prosthetic silicone liner having a 5–9 mm wall thickness. The present invention additionally contemplates a liner wall thickness of 5–9 mm.

This gap will later be filled with an injected liquid silicone material and cured to form the silicone liner according to the present invention. The inner, negative cavity of the aluminum block is polished and plated. Holes are drilled, strategically, in order to achieve proper silicone filling of the overall mold when it is clamped together over the inner core model. Vents (additional holes) are also added to facilitate the silicone filling process. Additional lengthening sections of the female mold must also be fabricated to accommodate the various lengths of the inner core model. The lowest section of the female mold is adapted to accept the umbrella 67 (FIGS. 6 and 7). The lowest section can also be capped when the umbrella 67 option is not required by an amputee user.

A custom-designed clamping station is constructed to hold and exert high pressures upon the metal mold. Prior art molds typically are injected with liquid silicone when in a vertical orientation. The present invention, with its anatomical shape and flexion angle selected from 20 to 60 degrees, preferably is injected in a horizontal orientation to ensure proper filling of the mold cavity with liquid silicone.

The injection molding procedure involves moving a two part, high-strength, highly flexible (when cured), heat-cured liquid silicone into the female mold from an outside port which fills the gap around the inner core model. A heater core is placed into the core model and it is heated to properly and rapidly cure the silicone material. Pressure is exerted onto the female mold by a custom-made clamping station which may be in excess of 30 tons simultaneously with the injection process. This method of fabricating a liner according to the present invention will produce a high-strength, optically-clear, thin-walled silicone liner. The liquid silicone material cures typically in 10–15 minutes. The heater core is then turned off, the clamping station is opened, the female mold is separated and the silicone liner is unrolled off the inner core model.

Another novel feature of the present invention is an anti-bacterial agent mixed in with the liner material. This anti-bacterial agent in the liner substantially suppresses the growth of bacteria between the liner and the residuum. During fabrication, as disclosed above. of the liner an anti-bacterial agent or combination of anti-bacterial agents such as "NEOSPORIN," "BACITRACIN" or "SILVEDENE" is added to the liner material. When the liner is placed over the residuum, the anti-bacterial agent in the liner material is slowly released by the chemical composition of the polymer which may be altered to effect precise control of the release of the anti-bacterial agents. As prosthetic silicone liners typically have a useful life of only six months to one year, it is envisioned that the anti-bacterial agent(s), contained within its silicone structure, offer a similar time of release. The moisture from perspiration always present on the residuum (within the prosthetic silicone liner) actually serves as the vehicle to move the anti-bacterial agent(s) from the silicone material to the skin in order to control bacteriological over-population. Without moisture (a solution) the anti-bacterial agent(s) would never reach the skin of the residuum. The movement of the anti-bacterial agent(s) from the prosthetic silicone liner to the residuum occurs as a consequence of entropy, that is, the anti-bacterial agent(s) will move from areas of greater concentration (within the silicone) to areas of lesser concentration (the skin). In this way the present invention further enhances the comfort, health and continued function of the amputee while also extending the useful life of the prosthesis liner.

The present invention, therefore, is well adapted to carry out the objects and attain the ends and advantages mentioned, as well as others inherent therein. While presently preferred embodiments of the invention and various aspects thereto has been given for purposes of disclosure, numerous changes in the details of construction, interconnection and arrangement has been described in connection with the preferred embodiments, it is not intended to be limited to the specific form set forth herein, but on the contrary, it is intended to cover such alternatives, modifications, and equivalents, as can be reasonably included within the spirit and scope of the invention as defined by the appended claims.

What is claimed is:

1. A below knee amputee prosthesis liner, comprising:

a molded polymer-like liner for fitting over a below knee amputation limb of a person;

said liner having a lower portion with a closed distal end, a knee portion and an upper portion having an opening adapted for insertion of a residuum of the amputee;

said lower portion being tapered wherein the distal end of said lower portion is narrower than the lower portion proximate to said knee portion;

said liner comprising a material having a time released anti-bacterial agent in the material;

said knee portion having a pre-flexed angle;

an umbrella shaped flexible shuttle housing integral with the closed distal end of said lower portion of said liner; and said shuttle housing having a coupling adapted for attachment to a rod which is part of a prosthesis.

2. The prosthesis liner of claim 1, further comprising a thickened band in a wall of said upper portion of said liner and biased toward the opening thereof.

3. The prosthesis liner of claim 1, further comprising at least two thickened bands in a wall of said upper portion of said liner and biased toward the opening thereof.

4. The prosthesis device of claim 3, wherein said at least two thickened bands are spaced ¾ inch apart.

5. The prosthesis liner of claim 3, wherein one of said at least two thickened bands may be trimmed off to shorten said upper portion of said liner.

6. The prosthesis liner of claim 1, wherein said time released anti-bacterial agent is selected from the group consisting of "NEOSPORIN," "BACITRACIN" or "SILVEDENE."

7. The prosthesis liner of claim 1, wherein said pre-flexed elected from twenty to sixty degrees.

8. The prosthesis liner of claim 1, wherein said taper is selected from five to twelve degrees.

9. The prosthesis liner of claim 1, wherein said liner is made of flexible and clear heat-cured two part silicone.

10. The prosthesis liner of claim 1, wherein said coupling is threaded.

11. The prosthesis liner of claim 1, wherein said shuttle housing is generally circular in shape with a series of oval openings evenly spaced and extending around the circular shape thereof.

12. The prosthesis liner of claim 1, wherein said flexible shuttle housing is made of silicone.

* * * * *